United States Patent
Ricketts

(10) Patent No.: US 10,384,601 B1
(45) Date of Patent: Aug. 20, 2019

(54) OPERATOR FEEDBACK SYSTEM

(71) Applicant: Honda Motor Co., Ltd., Tokyo (JP)

(72) Inventor: Brandon E. Ricketts, Marysville, OH (US)

(73) Assignee: Honda Motor Co., Ltd., Tokyo (JP)

( * ) Notice: Subject to any disclaimer, the term of this patent is extended or adjusted under 35 U.S.C. 154(b) by 0 days.

(21) Appl. No.: 16/003,426

(22) Filed: Jun. 8, 2018

(51) Int. Cl.
*B60Q 9/00* (2006.01)
*B60W 40/08* (2012.01)

(52) U.S. Cl.
CPC ........ *B60Q 9/00* (2013.01); *A61B 2562/0219* (2013.01); *B60W 40/08* (2013.01)

(58) Field of Classification Search
None
See application file for complete search history.

(56) References Cited

U.S. PATENT DOCUMENTS

| | | | |
|---|---|---|---|
| 7,266,471 B2 | 9/2007 | Jitsui et al. | |
| 7,313,467 B2 | 12/2007 | Breed et al. | |
| 8,258,934 B2 | 9/2012 | Filev et al. | |
| 8,630,768 B2 * | 1/2014 | McClellan | G01S 5/0027 701/36 |
| 9,477,639 B2 | 10/2016 | Fischer et al. | |
| 2006/0253240 A1 * | 11/2006 | Rao | B60W 50/0205 701/48 |
| 2012/0053805 A1 | 3/2012 | Dantu | |
| 2015/0210287 A1 * | 7/2015 | Penilla | B60W 40/08 701/49 |
| 2016/0110650 A1 | 4/2016 | Basir et al. | |
| 2018/0324565 A1 * | 11/2018 | Belagal Math | G08G 1/096791 |

FOREIGN PATENT DOCUMENTS

EP         2762363 A1    8/2014

* cited by examiner

*Primary Examiner* — Leon Viet Q Nguyen
(74) *Attorney, Agent, or Firm* — Honda Patents & Technologies North America, LLC; Clifford B Vaterlaus

(57) ABSTRACT

An operator feedback system of a vehicle includes an inertial measurement unit (IMU) and control circuitry. The inertial measurement unit (IMU) is integrated in one or more components of the vehicle. The IMU is configured to measure one or more acceleration parameters of the one or more components along one or more axes of the IMU. The control circuitry is configured to compare the one or more measured acceleration parameters to one or more preset limiting acceleration parameters. Further, the control circuitry is configured to notify an operator of the vehicle based on the measured one or more acceleration parameters exceeding the one or more preset limiting acceleration parameters.

19 Claims, 3 Drawing Sheets

OPERATOR FEEDBACK SYSTEM

TECHNICAL FIELD

The present disclosure generally relates to driver assistance systems for vehicles. More particularly, the present disclosure relates to an operator feedback system for determining acceleration experienced by one or more rear passengers of a vehicle and subsequently notifying an operator of the vehicle.

BACKGROUND

Currently, passenger cars increasingly use driver assistance systems such as Advanced Driver Assistance systems (ADAS) to minimize driver error and improve general driving behavior. ADAS may include several sub systems, for example, Hill Descent Control (HDC), Anti-lock Braking systems (ABS), Electronic Stability Program (ESP), parking assist, adaptive cruise control, lane assist, etc., employing a plurality of sensors. In general, such systems aid an operator or driver of a vehicle in avoiding collisions and improving ride comfort. However, in evaluating ride comfort, existing systems generally assess attributes corresponding to improved ride comfort from the perspective of the operator or driver alone.

Typically, in all-terrain vehicles (ATVs) with two rows of seating, rear passengers experience a different level of comfort than the operator or front passenger of the vehicle. Consequently, differing perceptions create a gap in the understanding of the severity of driving style for the operator. For instance, the driver may often cross obstacles at a speed that is comfortable for the front seat but may be unaware that the rear passengers are much less comfortable. Alternately, while passing through routes having continuously winding roads, the driver may negotiate bends or curves at excessive speed. In the case of a timid rear passenger or a child, they may not communicate to the driver to slow down or to alter his/her driving style. In such cases, the rear passenger may experience discomfort. Consequently, the rear passengers experience a reduced enjoyment of the ride. As such, a mechanism or device that detects instantaneous acceleration experienced by the rear passengers and subsequently notifies the driver of the vehicle is desired.

In recent years, large technological advances have been made in the field of driverless or autonomous vehicles. Typically, autonomous vehicles rely on a plurality of sensory inputs to achieve situational and self-awareness. Despite the obvious advantages of employing driverless vehicles, the perceived lack of control on the part of passengers have posed significant concerns. As such, a feedback system controllable by passengers that modify acceleration of autonomous vehicles based on perceived passenger discomfort is therefore desirable. Further, such a feedback system must not be prohibitively expensive to produce and implement.

Hence, there is a long felt but unresolved need for a device, which instantaneously detects acceleration experienced by the rear passengers and subsequently notifies the driver of the vehicle. Furthermore, there is a need for a feedback system controllable by passengers that modify acceleration of autonomous vehicles based on perceived passenger discomfort.

SUMMARY

This summary is provided to introduce a selection of concepts in a simplified form that are further disclosed in the detailed description of the present disclosure. This summary is not intended to identify key or essential inventive concepts of the claimed subject matter, nor is it intended for determining the scope of the claimed subject matter.

An operator feedback system of a vehicle, disclosed herein, comprises an inertial measurement unit (IMU) and control circuitry. The inertial measurement unit (IMU) is integrated in one or more interior components of the vehicle, for example, a seat, an armrest, a headrest, etc. Further, the IMU is configured to measure one or more acceleration parameters of the one or more interior components along one or more axes of the IMU. The control circuitry is configured to compare the one or more measured acceleration parameters to one or more preset limiting acceleration parameters. The control circuitry is further configured to notify an operator of the vehicle based on the measured one or more acceleration parameters exceeding the one or more preset limiting acceleration parameters.

A method for providing feedback to an operator of a vehicle uses the operator feedback system comprising the inertial measurement unit (IMU) and the control circuitry. The method, disclosed herein, comprises measuring via the IMU one or more acceleration parameters of one or more interior components along one or more axes of the IMU. Next, the control circuitry compares the measured one or more acceleration parameters to one or more preset limiting acceleration parameters. Finally, the operator feedback system notifies the operator of the vehicle based on the measured one or more acceleration parameters exceeding the one or more preset limiting acceleration parameters.

In accordance with an alternate embodiment, the method for providing feedback to an operator of a vehicle uses an operator feedback system comprising an accelerometer and control circuitry. The method, disclosed herein, comprises measuring, via the accelerometer one or more acceleration parameters of a rear passenger seating area of the vehicle along one or more axes of the accelerometer. Next, the control circuitry compares the measured one or more acceleration parameters to one or more preset limiting acceleration parameters. Finally, the operator feedback system notifies the operator of the vehicle when the one or more acceleration parameters exceed the one or more preset limiting acceleration parameters.

BRIEF DESCRIPTION OF THE DRAWINGS

The foregoing summary, as well as the following detailed description of the present disclosure, is better understood when read in conjunction with the appended drawings. For the purpose of illustrating the present disclosure, exemplary constructions of one or more embodiments are shown in the drawings. However, the present disclosure is not limited to the specific methods and structures disclosed herein. The description of a method step or a structure referenced by a numeral in a drawing is applicable to the description of that method step or structure shown by that same numeral in any subsequent drawing herein.

DETAILED DESCRIPTION OF THE PREFERRED EMBODIMENT

Advanced driver assistance systems (ADAS) are systems that aid an operator or driver of a vehicle during a trip.

Typically, ADAS systems function to improve car operation. However, ADAS may also be construed to include any type of additional electronic device that provides driver assistance or helps optimize driver behavior. In the present disclosure, the operator feedback system may function as part of the ADAS system of the vehicle.

When the vehicle is in motion, both rear passenger(s) and driver are subjected to a plurality of physical forces, for example, vibrations, inertial forces, g-force, lateral acceleration, etc. Sometimes, the driver may experience physical forces that are less uncomfortable than the physical forces experienced by the rear passenger(s). According to an aspect of an exemplary embodiment of the present disclosure, the operator feedback system detects one or more acceleration parameters of one or more interior components of the vehicle. As used herein, "acceleration parameters" refer to a plurality of physical forces comprising, for example, g-force during linear acceleration, g-force during linear deceleration, g-force during turning, longitudinal acceleration, lateral acceleration, etc. The operator feedback system compares the detected one or more acceleration parameters to one or more preset limiting acceleration parameters. As used herein, "preset limiting acceleration parameters" refer to a limiting acceleration parameter value set by the rear passengers or the operator of the vehicle. The acceleration parameter value corresponds to any of the acceleration parameters as defined above. For instance, if the rear passengers deem an acceleration of 0.6 g uncomfortable, the rear passengers may set the preset limiting acceleration parameter as 0.6 g. If the detected one or more acceleration parameters exceed the one or more preset limiting acceleration parameters, the operator feedback system notifies the operator via an audio, visual, or an audio-visual notification. The operator feedback system may alert the operator until the acceleration is reduced. Alternatively, the driver or operator may be required to clear the notification. In one embodiment, high acceleration events that occur over a very short duration, for example, ranging from a few milliseconds to a few seconds would be sensed and communicated to the driver via a notification. The driver or operator may be required to clear the notification. Clearing the notification may be a necessary requirement as the driver or operator might not notice the short notification if the operator feedback system terminated the notification once the acceleration was reduced.

Figure 1:
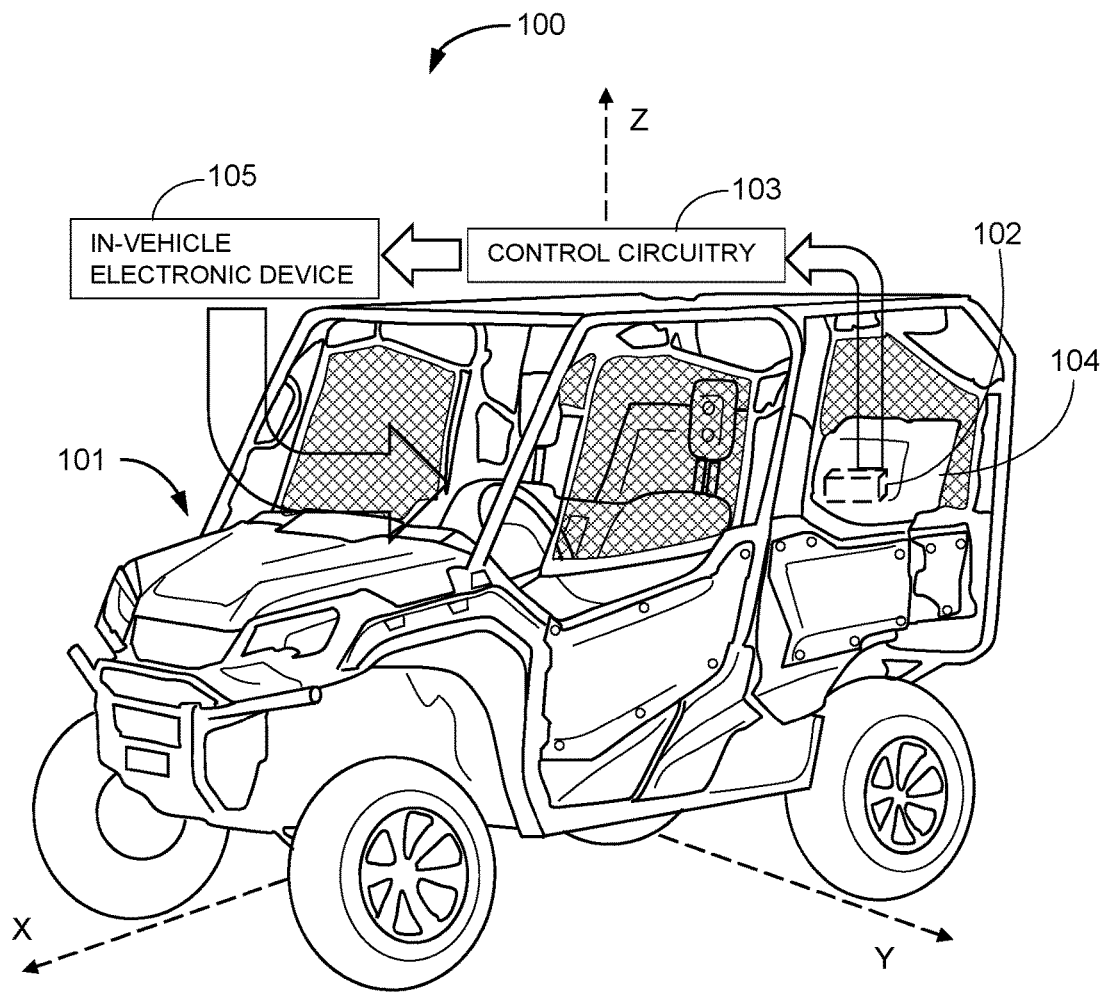
FIG. 1 exemplarily illustrates a perspective view of an embodiment of an operator feedback system implemented in a vehicle.

FIG. 1 exemplarily illustrates a perspective view of an embodiment of an operator feedback system 100 implemented in a vehicle 101. The operator feedback system 100 of a vehicle 101 comprises an inertial measurement unit (IMU) 102 and a control circuitry 103. In an embodiment of the present disclosure, the vehicle 101 may include an all-terrain vehicle (ATV) such as a quad, quad bike, three-wheeler, four-wheeler, quadricycle, or the like as defined by the American National Standards Institute (ANSI), a Utility Task Vehicle (UTV)/Side by side (S×S)/Recreational Off-Highway Vehicle (ROHV)/Multipurpose Off Highway Utility Vehicle (MOHUV) as defined by the Recreational Off-Highway Association (ROHVA), a van, a station wagon, etc. The inertial measurement unit (IMU) 102 is operatively connected to the control circuitry 103. Moreover, the IMU 102 is integrated in one or more interior components 104 of the vehicle 101. As used herein, "inertial measurement unit (IMU)" refers to an electronic device comprising a combination of accelerometers, gyroscopes, magnetometers, etc., that measure and report a specific force, angular rate, and sometimes the magnetic field surrounding the interior components 104 of the vehicle 101. In the present disclosure, the IMU 102 may also be construed to refer to an electronic device having only an accelerometer. Additionally, the IMU 102 may also refer to an IMU embedded within a Global Positioning System (GPS) enabled electronic device. An IMU allows a GPS receiver to work when GPS-signals are unavailable, such as in tunnels, inside buildings, when electronic interference is present, etc.

The passengers of the vehicle 101 are subjected to several forces along the X, Y, and Z-axes as exemplarily illustrated in FIG. 1. For instance, when the vehicle 101 is in motion, the passengers experience physical forces along the Z-axis due to vibrations caused while travelling over rough terrain. Alternately, the passengers may experience physical forces along the X-axis due to acceleration or deceleration of the vehicle 101. Similarly, the passengers may experience physical forces along the Y-axis due to steering while negotiating curves or bends on the road. As such, the passengers may be subject to physical forces along one or more of the X, Y, and Z-axes. In an embodiment, the inertial measurement unit (IMU) 102 is operatively connected to the control circuitry 103. The IMU 102 is configured to measure one or more acceleration parameters of the one or more interior components 104 along one or more axes of the IMU 102.

The control circuitry 103 may comprise a microprocessor, suitable logic, circuits, interfaces, or the like. The control circuitry 103 is configured to compare the one or more measured acceleration parameters of the interior components 104 to one or more preset limiting acceleration parameters. In accordance with an embodiment, the one or more interior components 104 comprise one of an armrest, a backrest, a seating cushion insert of a seating equipment, and suitable rear passenger seating area components. Further, the control circuitry 103 is configured to notify an operator of the vehicle 101 based on the measured one or more acceleration parameters exceeding the one or more preset limiting acceleration parameters. Moreover, the rear passengers or the operator may modify the one or more preset limiting acceleration parameters depending on individual comfort.

In accordance with an embodiment, the operator feedback system 100 further comprises an in-vehicle electronic device 105 configured to report one of the one or more measured acceleration parameters and the one or more preset limiting acceleration parameters to one or more passengers of the vehicle. The in-vehicle electronic device 105 may generate an audio notification, a visual notification, or an audio-visual notification. The in-vehicle electronic device 105 may be implemented as a driver vehicle interface (DVI), in-vehicle infotainment (IVI) system, an electronic control unit (ECU), or the like. In accordance with an embodiment, the operator feedback system 100 may further comprise additional sensors such as a load sensor, an image-processing sensor, a proximity sensor, a motion sensor, a seat belt position sensor or the like configured to detect a presence of the passengers in the vehicle 101. In such an embodiment, the inertial measurement unit (IMU) 102 may be configured to detect acceleration parameters of the interior components 104 of the vehicle 101 only if the sensors detect the presence of the passengers in the vehicle 101.

Figure 2:
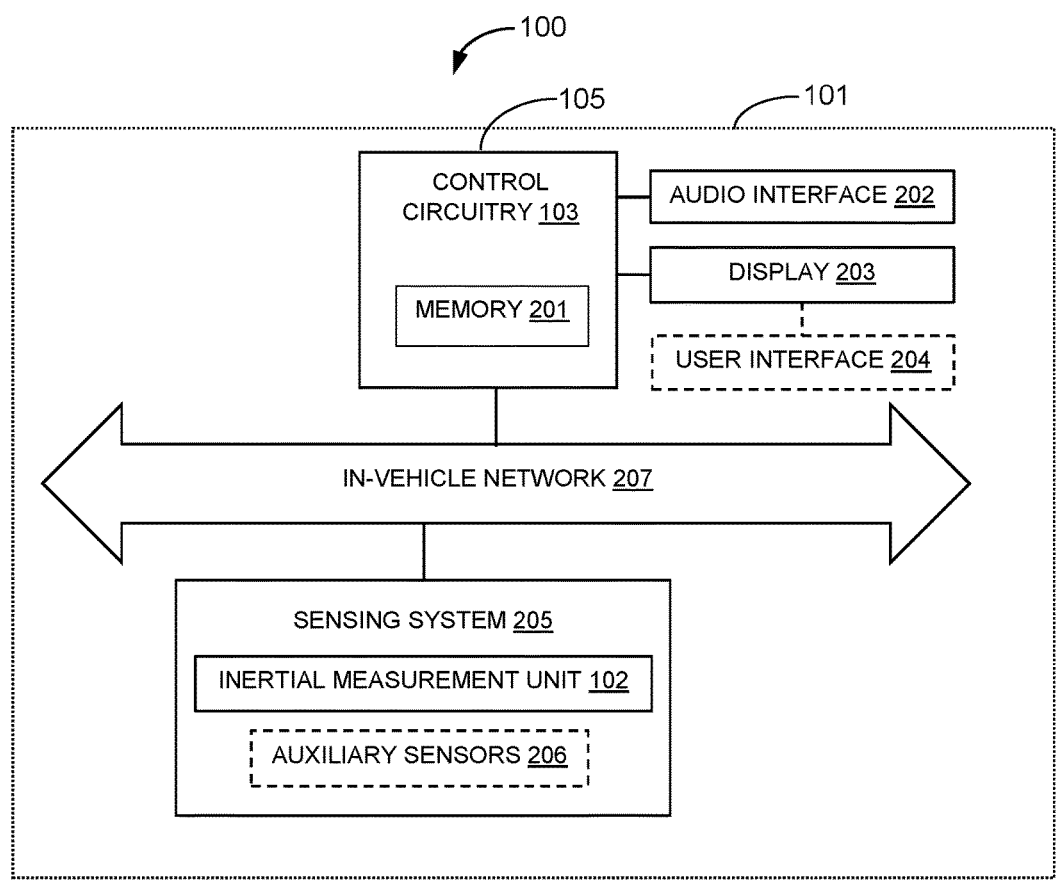
FIG. 2 exemplarily illustrates a block diagram of an embodiment of an operator feedback system.

FIG. 2 exemplarily illustrates a block diagram of an embodiment of an operator feedback system 100. The operator feedback system 100 of the vehicle 101 comprises an inertial measurement unit (IMU) 102 and control circuitry 103. The IMU 102 is integrated in one or more interior components 104 of the vehicle 101. The IMU 102 is configured to measure one or more acceleration parameters of the one or more interior components 104 along one or more axes of the IMU 102 as exemplarily illustrated in FIG. 1. In an embodiment, the IMU 102 may comprise only an accelerometer. Accelerometers are electromechanical devices that detect either static or dynamic forces, for example, gravity, vibrations, acceleration, etc. As such, accelerometers detect acceleration parameters along one, two, or three axes. In an embodiment, the accelerometer may be a single axis accelerometer, a dual axis accelerometer, or a triple axis accelerometer. Additionally, the accelerometer used may be a capacitive accelerometer, a potentiometric accelerometer, a piezoelectric accelerometer, a piezo-resistive accelerometer, a variable inductance accelerometer, a Hall-Effect accelerometer, a magneto resistive accelerometer, a fiber Bragg grating (FBG) accelerometer, a heated gas accelerometer, a Micro Electro-Mechanical Sensors (MEMS) based accelerometer, etc.

The operator feedback system 100 further comprises an in-vehicle electronic device 105. The in-vehicle electronic device 105 may be implemented as part of the in-vehicle infotainment (IVI) system, an electronic control unit (ECU), a driver vehicle interface (DVI), or the like. In an alternate embodiment, the in-vehicle electronic device 105 may include a tablet device, a touch responsive mobile device, or the like. The in-vehicle electronic device 105 may also be implemented in an autonomous vehicle. As such, the in-vehicle electronic device 105 may be configurable by a centralized server system. The in-vehicle electronic device 105 may further include control circuitry 103, comprising at least a microprocessor. The control circuitry 103 may include, but are not limited to a microcontroller, a Reduced Instruction Set Computing (RISC) processor, an Application-Specific Integrated Circuit (ASIC) processor, a Complex Instruction Set Computing (CISC) processor, a central processing unit (CPU), a graphics processing unit (GPU), a state machine, and/or other processors or circuits.

The control circuitry 103 may comprise suitable logic, circuits, interfaces, and/or code that may be configured to execute a set of instructions stored in a memory 201. The memory 201 may additionally store various types of information related to the vehicle 101 or preferences of the passengers, for example, preset limiting acceleration parameters preferred by passengers, driver behavior, historical data related to passenger preferences and driver behavior, etc. Examples of implementation of the memory 201 may include, but are not limited to, Electrically Erasable Programmable Read-only Memory (EEPROM), Random Access Memory (RAM), Read Only Memory (ROM), Hard Disk Drive (HDD), Flash memory, Solid-State Drive (SSD), and/or CPU cache memory. The in-vehicle electronic device 105 may further comprise an audio interface 202, a display 203, and a user interface 204. The control circuitry 103 compares the acceleration parameters measured by the inertial measurement unit (IMU) 102 to the preset limiting acceleration parameters stored in the memory 201. If the measured acceleration parameters exceed the preset limiting acceleration parameters, the in-vehicle electronic device 105 may generate the audio notification via the audio interface 202 or a visual indication via the display 203. The audio interface 202 may include, but is not limited to, speaker systems, integrated audio devices or the like.

The display 203 may comprise suitable logic, circuitry, interfaces, and/or code that may be configured to render various types of information and/or entertainment content via the user interface 204. In an embodiment, the display 203 may be a flashing visual indicator, such as a light emitting diode (LED) or the like. The user interface 204 may be a customized graphic user interface (GUI) configured to display vehicle information such as the preset limiting acceleration parameters, measured acceleration parameters, etc. The display 203 may include, but is not limited to a display of the driver vehicle interface (DVI), a display of the in-vehicle infotainment head unit, a projection based display, a heads-up display (HUD), an electro-chromic display, and/or holographic display. In other embodiments, the display 203 may be a touchscreen display, a tactile electronic display, and/or a touchable hologram. As such, the display 203 may be configured to receive inputs from the passenger or driver for setting or modifying the preset limiting acceleration parameters.

In an embodiment, the display 203 may be configured to render an audio-visual notification. As an additional feature to increase the usability, the preset limiting acceleration parameters could be adjustable depending on the level of discomfort the rear passengers are willing to accept. This could be done through an embodiment of the display 203 for example, an infotainment system, a dial on the dash, or even by the rear passengers themselves via a mobile device. Considering rear passenger adjustment of the operator feedback system 100, a live readout of the g sensor or accelerometer of the inertial measurement unit (IMU) could be displayed to the rear passengers as they ride via the display 203. This would give them a better understanding of the accelerations that they are feeling and better help them to understand what they can accept and set the preset limiting acceleration parameters accordingly. As an insurance that the driver sees the warning indication, it could be required that the driver must clear the message on the display 203 to regain normal indication. Additionally, once the control circuitry 103 generates the audio notification or visual notification via the audio interface 202 or the display 203, the driver or operator may be required to clear the audio or visual notification. Alternately, the audio notification, the visual notification, or the audio-visual notification is configured to stop only based on an input received from the operator via the display 203. Consequently, the control circuitry 103 configures the audio interface 202 or the display 203 to return to a normal indication mode.

In some embodiments, the control circuitry 103 may be configured to automatically control one or more components or systems, for example, the in-vehicle electronic device 105, the sensing system 205, etc. The sensing system 205 comprises the inertial measurement unit (IMU) 102 and a plurality of auxiliary sensors 206. The auxiliary sensors 206 are configured to detect a presence of the passengers in the vehicle 101. The plurality of auxiliary sensors 206 may comprise one or a combination of a load sensor, an image-processing sensor, a proximity sensor, a motion sensor, and a seat belt position sensor. The image-processing sensor may be configured to capture a plurality of images of the interior of the vehicle 101. Further, the in-vehicle electronic device 105 may be configured to receive the captured images via an in-vehicle network 207. The in-vehicle electronic device 105 may be configured to analyze the received images to detect the presence of passengers in the rear seating equipment of the vehicle 101. The presence of the passengers may be confirmed by applying different image processing techniques, for example, face detection, foreground/background segregation, and the like. In an alternate embodiment of the present disclosure, the load sensor may be used in conjunction with the image-processing sensor to detect the presence of the passengers.

Several known occupancy detection techniques may be employed in association with the image-processing sensor, for example, an augmented passive infrared (PIR) based sensing technique, $CO_2$ based occupancy detection techniques, or microphone based occupancy detection, or the like as will be evident to one skilled in the art. In alternate embodiments, the load sensor may be employed in weight sensing systems to detect the presence of the passengers. For example, a pressure sensor may be installed in the rear passenger seats. Once the passenger(s) occupies the seat, the pressure sensor detects the change in weight. An additional strain gauge sensor may measure the cinching force of the seatbelt to confirm the presence of the passenger in the rear seat. One or a combination of the detection techniques mentioned above may be employed to confirm the presence of the passengers. In an embodiment, confirmation of the presence of occupants may be a prerequisite for the inertial measurement unit (IMU) 102 to detect the one or more acceleration parameters as disclosed in the detailed description of FIG. 1.

The sensing system 205 may communicate with the control circuitry 103 via the in-vehicle network 207. The in-vehicle network 207 may include, for example, a controller area network (CAN), a Bluetooth Low Energy (BLE) network, a vehicle area network (VAN), Domestic Digital Bus (D2B), Time-Triggered Protocol (TTP), Flex Ray, IEEE 1394, Carrier Sense Multiple Access With Collision Detection (CSMA/CD) based data communication protocol, Inter-integrated Circuit (I2C), Inter Equipment Bus (IEBus), Society of Automotive Engineers, (SAE) J1708, SAE J1939, International Organization for Standardization (ISO) 11992, ISO 11783, Power-line communication (PLC), Plastic Optic Fiber (POF), Serial Peripheral Interface (SPI) bus, Local Interconnect Network (LIN), etc.

Figure 3:
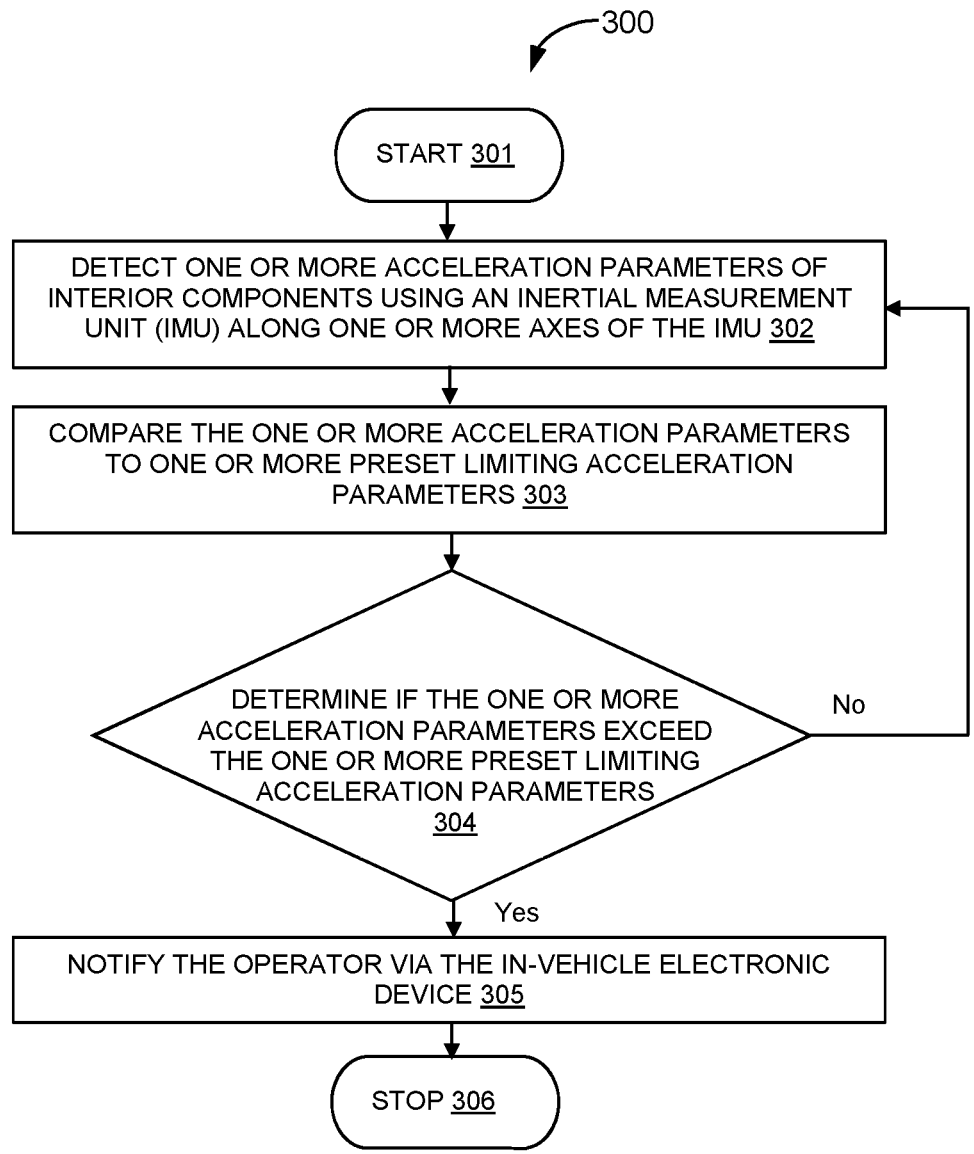
FIG. 3 exemplarily illustrates a flowchart showing a method of providing feedback to an operator of a vehicle.

FIG. 3 exemplarily illustrates a flowchart showing a method 300 of providing feedback to an operator of a vehicle 101. The following detailed description must be read in conjunction with the drawings and detailed descriptions of FIGS. 1-2. In the method, disclosed herein, the operations of operator feedback system 100 disclosed in the detailed descriptions of FIGS. 1-2 begin at Step 301 and proceed to Step 302. The operator feedback system 100 of a vehicle 101 comprises an inertial measurement unit (IMU) 102 and a control circuitry 103. The IMU 102 is operatively connected to the control circuitry 103. Moreover, the IMU 102 is integrated in one or more interior components 104 of the vehicle 101.

At Step 302, the inertial measurement unit (IMU) 102 detects one or more acceleration parameters of interior components 104 along one or more axes of the IMU 102. The IMU 102 is integrated into the interior components 104, for example, rear seats or rear seating area, an armrest, etc., and measures the one or more acceleration parameters when the vehicle 101 is in motion. In an embodiment, the IMU 102 is configured to measure the one or more acceleration parameters of the one or more interior components only if one or more sensors detect the presence of the one or more passengers in the vehicle. The one or more sensors may include a load sensor, an image-processing sensor, a proximity sensor, a seat belt position sensor, a motion sensor or a combination of any of the sensors.

At Step 303, the control circuitry 103 compares the measured one or more acceleration parameters to one or more preset limiting acceleration parameters. Further, the operator feedback system 100 is configured to report one of the one or more measured acceleration parameters and the one or more preset limiting acceleration parameters to the one or more passengers of the vehicle via the in-vehicle electronic device 105. In an embodiment, the one or more preset limiting acceleration parameters are configured to be modified by the one or more passengers present in the rear passenger seating area.

At Step 304, the control circuitry 103 of the operator feedback system 100 determines whether the one or more acceleration parameters exceed the one or more preset limiting acceleration parameters. If the acceleration parameters are higher than the preset limiting acceleration parameters, control passes to Step 305. In other cases, the control returns to Step 302.

At Step 305, when the preset limiting acceleration parameters is exceeded, the control circuitry 103 notifies the operator of the vehicle 101 via an in-vehicle electronic device 105. In an embodiment, the control circuitry 103 may notify the operator or driver using the audio notification, a visual notification, or an audio-visual notification. For instance, the control circuitry 103 may configure the in-vehicle electronic device 105 to display an alert message or an alarm. Alternately, the control circuitry 103 may employ a light emitting diode (LED) to flash a warning to the operator via an indicator light or infotainment system that alerts the operator. In an embodiment, the audio notification, the visual notification, and the audio-visual notification is configured to stop based on an input received from the operator via the control circuitry 103.

In an embodiment, the operator feedback system 100 is implemented in an all-terrain vehicle as disclosed in the detailed description of FIG. 1. However, several other embodiments of the present disclosure may be implemented using other vehicles, for example, a bus, a passenger car, a Sport Utility Vehicle (SUV), a Multi-utility vehicle (MUV)/Utility Task Vehicle (UTV)/Side by side (S×S)/Recreational Off-Highway Vehicle (ROHV)/Multipurpose Off Highway Utility Vehicle (MOHUV) as defined by the Recreational Off-Highway Association (ROHVA), a van, a station wagon, etc. Alternately, the operator feedback system 100 may be implemented in a vehicle 101 that is part of an autonomous or a semi-autonomous fleet. As used herein, "the autonomous or semi-autonomous fleet" may implement known autonomous or semi-autonomous control methods, wherein a vehicle is equipped with devices capable of locating the vehicle and utilizing control methods that are employed to augment or substitute driver control of the vehicle. As such, the inertial measurement unit (IMU) 102 may be configured to detect and transmit the one or more acceleration parameters to a remote server or fleet management system that is part of the operator feedback system 100 via a wireless communication network. In such an embodiment, the remote server or the fleet management system may function as the autonomous or semi-autonomous "operator" of the operator feedback system 100. Further, the fleet management system may be configured to receive preset limiting acceleration parameters from potential passengers (both front and rear) indicating their preference from an electronic device such as a handheld mobile device via the wireless communication network. The wireless communication network may include, but is not limited to, a Wide Area Network (WAN), a cellular network, such as a 3G, 4G, or 5G network, an Internet-based mobile ad hoc networks (IMANET), etc. The remote server or fleet management system may further be configured to compare the measured acceleration parameters of a target vehicle to a preset limiting acceleration parameter preferred by a passenger of the target vehicle. Additionally, the remote server or fleet management system may be configured to adjust the acceleration parameters of the target vehicle to fall below the limiting acceleration parameter preferred by the passenger of the target vehicle.

In an embodiment, the operator feedback system 100 implemented in an autonomous or semi-autonomous fleet may utilize a Global Positioning System (GPS) to determine a location where a passenger preference of the preset limiting acceleration parameter was exceeded and communicate the location to the fleet management system or remote server. It will be appreciated that several location estimation techniques may be utilized to determine the location where the passenger preference was exceeded. For instance, the operator feedback system 100 may be configured to utilize image recognition methods, data transmitted by proximal vehicles that are part of the fleet, landmarks, road features, or other recognizable images to estimate the vehicle location and orientation where the passenger preference was exceeded. Alternately, GPS data can be utilized in coordination with 3D map data to approximate the location of the vehicle at which the passenger preference was exceeded. As such, the operator feedback system 100 may be configured to remember the location. At the next instance when the vehicle is near the location, the acceleration parameters of the vehicle may be controlled to achieve the preset passenger preference.

The present disclosure may be realized in hardware, or a combination of hardware and software. The present disclosure may be realized in a centralized fashion, in at least one computer system, or in a distributed fashion, where different elements may be spread across several interconnected computer systems. A computer system or other apparatus adapted for carrying out the methods described herein may be suited. A combination of hardware and software may be a general-purpose computer system with a computer program that, when loaded and executed, may control the computer system such that it carries out the methods described herein. The present disclosure may be realized in hardware that comprises a portion of an integrated circuit that also performs other functions. It may be understood that, depending on the embodiment, some of the steps described above may be eliminated, while other additional steps may be added, and the sequence of steps may be changed.

The foregoing description of embodiments and examples has been presented for purposes of illustration and description. It is not intended to be exhaustive or limiting to the forms described. Numerous modifications are possible in light of the above teachings. Some of those modifications have been discussed and others will be understood by those skilled in the art. The embodiments were chosen and described for illustration of various embodiments. The scope is, of course, not limited to the examples or embodiments set forth herein, but can be employed in any number of applications and equivalent devices by those of ordinary skill in the art. Rather it is hereby intended the scope be defined by the claims appended hereto. Additionally, the features of various implementing embodiments may be combined to form further embodiments of the invention.

What is claimed is:

1. An operator feedback system of a vehicle for reporting acceleration experienced by one or more passengers in a rear passenger seating area to an operator of the vehicle, the operator feedback system comprising:
   an inertial measurement unit (IMU) integrated in one or more components of the vehicle in the rear passenger seating area, the IMU configured to measure one or more acceleration parameters of the one or more components along one or more axes of the IMU;
   an in-vehicle electronic device that reports the one or more measured acceleration parameters and one or more preset limiting acceleration parameters to the operator and the one or more passengers of the vehicle; and
   a control circuitry configured to:
   compare the one or more measured acceleration parameters to the one or more preset limiting acceleration parameters; and
   notify the operator of the vehicle via the in-vehicle electronic device based on the one or more measured acceleration parameters exceeding the one or more preset limiting acceleration parameters;
   wherein the one or more preset limiting acceleration parameters are configured to be modified by the one or more passengers or the operator of the vehicle.

2. The operator feedback system according to claim 1, wherein notifying the operator comprises generating one of an audio notification, a visual notification, and an audio-visual notification via the control circuitry.

3. The operator feedback system according to claim 2, wherein the one of the audio notification, the visual notification, and the audio-visual notification is configured to be cleared based on an input received from the operator via the control circuitry, after which time the in-vehicle electronic device resumes to a normal indication without the one of the audio notification, the visual notification, and the audio-visual notification until the one or more measured acceleration parameters exceeds the one or more preset limiting acceleration parameters again.

4. The operator feedback system according to claim 1, further comprising one or more sensors configured to detect a presence of the one or more passengers in the vehicle, wherein the IMU is configured to measure the one or more acceleration parameters of the one or more components only if the one or more sensors detects the presence of the one or more passengers in the vehicle.

5. The operator feedback system according to claim 4, wherein the one or more sensors comprise one or a combination of a load sensor, an image-processing sensor, a proximity sensor, a motion sensor, and a seat belt position sensor.

6. The operator feedback system according to claim 1, wherein the one or more components comprise one of an armrest, a backrest, a seating cushion insert of a seating equipment, and a rear passenger seating area component.

7. A method for providing feedback to an operator of a vehicle of accelerations experienced by one or more passengers in a rear passenger seating area of the vehicle, the method comprising:
   measuring, via an inertial measurement unit (IMU) in the rear passenger seating area, one or more acceleration parameters of one or more interior components along one or more axes of the IMU;
   comparing, via a control circuitry, the one or more measured acceleration parameters to one or more preset limiting acceleration parameters modifiable by the one or more passengers in the rear passenger seating area of the vehicle;
   reporting the one or more measured acceleration parameters and the one or more preset limiting acceleration parameters to the operator and the one or more passengers of the vehicle; and
   notifying the operator of the vehicle based on the one or more measured acceleration parameters exceeding the one or more preset limiting acceleration parameters.

8. The method according to claim 7, further comprising detecting a presence of the one or more passengers in the vehicle via one or more sensors.

9. The method according to claim 8, wherein the IMU is configured to measure the one or more acceleration parameters of the one or more interior components only when the one or more sensors detects the presence of the one or more passengers in the vehicle.

10. The method according to claim 8, wherein the one or more sensors comprise one or a combination of a load sensor, an image-processing sensor, a proximity sensor, a seat belt position sensor, and a motion sensor.

11. The method according to claim 7, further comprising reporting the one or more measured acceleration parameters and the one or more preset limiting acceleration parameters to the one or more passengers of the vehicle, via an in-vehicle electronic device.

12. The method according to claim 7, wherein notifying the operator comprises generating one of an audio notification, a visual notification, and an audio-visual notification via the control circuitry.

13. The method according to claim 12, wherein the one of the audio notification, the visual notification, and the audio-visual notification is configured to be cleared based on an input received from the operator via the control circuitry, after which time the in-vehicle electronic device resumes to a normal indication without the one of the audio notification, the visual notification, and the audio-visual notification until the one or more measured acceleration parameters exceeds the one or more preset limiting acceleration parameters again.

14. The method according to claim 7, wherein the IMU is one of a single axis accelerometer, a dual axis accelerometer, and a triple axis accelerometer.

15. A method for providing feedback to an operator of a vehicle of accelerations experienced by one or more passengers in a rear passenger seating area of the vehicle, the method comprising:
   measuring, via an accelerometer in the rear passenger seating area, one or more acceleration parameters of the rear passenger seating area of the vehicle along one or more axes of the accelerometer;
   comparing, via a control circuitry, the one or more measured acceleration parameters to one or more preset limiting acceleration parameters modifiable by the one or more passengers seated in the rear passenger seating area;
   reporting the one or more measured acceleration parameters and the one or more preset limiting acceleration parameters to the operator and the one or more passengers of the vehicle; and
   notifying the operator of the vehicle when the one or more measured acceleration parameters exceed the one or more preset limiting acceleration parameters.

16. The method according to claim 15, further comprising detecting when the one or more passengers are seated in the rear passenger compartment, and wherein the accelerometer is configured to measure the one or more acceleration parameters of the rear passenger seating area only when the one or more passengers are present in the rear passenger seating area.

17. The method according to claim 16, wherein the notification that the one or more measured acceleration parameters exceeds the one or more preset limiting acceleration parameters is cleared based on an input received from the operator, after which time a normal indication resumes without the notification until the one or more measured acceleration parameters exceeds the one or more preset limiting acceleration parameters again.

18. The operator feedback system according to claim 3, wherein the one or more preset limiting acceleration parameters are configured to be modified by the operator of the vehicle and the one or more passengers.

19. The operator feedback system according to claim 1, wherein the one or more preset limiting acceleration parameters are configured to be modified by the operator and the one or more passengers;
   wherein notifying the operator comprises generating one of an audio notification, a visual notification, and an audio-visual notification via the control circuitry;
   wherein the one of the audio notification, the visual notification, and the audio-visual notification is configured to be cleared based on an input received from the operator via the control circuitry, after which time the in-vehicle electronic device resumes to a normal indication without the one of the audio notification, the visual notification, and the audio-visual notification until the one or more measured acceleration parameters exceeds the one or more preset limiting acceleration parameters again;
   wherein the operator feedback system further comprises one or more sensors configured to detect a presence of the one or more passengers in the vehicle, wherein the IMU is configured to measure the one or more acceleration parameters of the one or more components only if the one or more sensors detects the presence of the one or more passengers in the vehicle;
   wherein the one or more sensors comprise one or a combination of a load sensor, an image-processing sensor, a proximity sensor, a motion sensor, and a seat belt position sensor; and
   wherein the one or more components comprise one of an armrest, a backrest, a seating cushion insert of a seating equipment, and a rear passenger seating area component.

* * * * *